United States Patent [19]

Leinert

[11] Patent Number: 4,697,022
[45] Date of Patent: Sep. 29, 1987

[54] PROCESS FOR THE PREPARATION OF OPTICALLY-ACTIVE CARBAZOLE DERIVATIVES, NEW R- AND S-CARBAZOLE DERIVATIVES AND PHARMACEUTICAL COMPOSITIONS CONTAINING THESE COMPOUNDS

[75] Inventor: Herbert Leinert, Heppenheim, Fed. Rep. of Germany

[73] Assignee: Boehringer Mannheim GmbH, Mannheim, Fed. Rep. of Germany

[21] Appl. No.: 612,255

[22] Filed: May 21, 1984

[30] Foreign Application Priority Data

May 26, 1983 [DE] Fed. Rep. of Germany ....... 3319027

[51] Int. Cl.[4] ............................................ C07D 209/88
[52] U.S. Cl. ................................................... 548/444
[58] Field of Search ......................... 548/444; 564/349

[56] References Cited

U.S. PATENT DOCUMENTS

| | | | |
|---|---|---|---|
| 4,085,136 | 4/1978 | Tucker | 564/349 |
| 4,202,978 | 5/1980 | Fahrenholtz et al. | 544/393 |
| 4,342,688 | 8/1982 | Tappe | 548/444 |
| 4,400,383 | 8/1983 | Davidson et al. | 548/444 |
| 4,411,913 | 10/1983 | Payne et al. | 564/349 |
| 4,503,067 | 3/1985 | Wiedemann et al. | 548/444 |

FOREIGN PATENT DOCUMENTS 1369580 10/1974 United Kingdom ................ 548/444

*Primary Examiner*—Glennon H. Hollrah
*Assistant Examiner*—Dara Dinner
*Attorney, Agent, or Firm*—Felfe & Lynch

[57] ABSTRACT

A process for the preparation of S- or R-carbazole derivatives of the general formula:

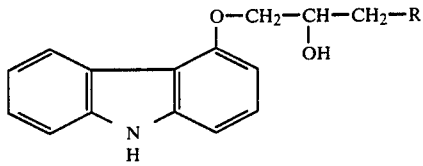

in which R is an unsubstituted or substituted amino radical and pharmacologically acceptable salts, by either reacting R-(−)-epichlorohydrin (for the S-carbazole derivative); or reacting an S-epoxide derivative of the general formula:

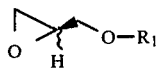

in which $R_1$ is the residue of a substituted sulphonic acid derivative (for the R-carbazole derivative); with 4-hydroxycarbazole and then with ammonia or a substituted amine of the general formula RH, and recovering the compound or converting it to a pharmacologically acceptable salt.

The new R-(+)- and S(−)-carbazole derivatives provided by the inventive process have unexpected beta blocking and vasodilatory properties and are useful in pharmaceutical compositions. R-(+)-carbazole derivatives are also useful for the treatment of glaucoma.

2 Claims, No Drawings

PROCESS FOR THE PREPARATION OF OPTICALLY-ACTIVE CARBAZOLE DERIVATIVES, NEW R- AND S-CARBAZOLE DERIVATIVES AND PHARMACEUTICAL COMPOSITIONS CONTAINING THESE COMPOUNDS

The present invention is concerned with a process for the preparation of optically-active carbazole derivatives, with new R- and S-carbazole derivatives and with pharmaceutical compositions containing these compounds.

Thus, according to the present invention, there is provided an asymmetric synthesis, with high optical purity, of R- and S-carbazole derivatives of the general formula:

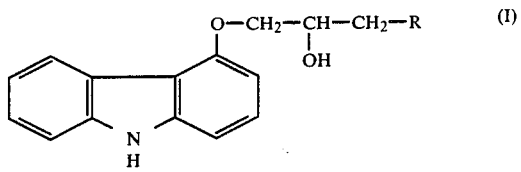

in which R is an unsubstituted or substituted amino radical, as well as of their pharmacologically acceptable salts.

In general formula (I), R is preferably an amino radical which is substituted by a lower alkyl radical, with up to 6 carbon atoms such as a methyl, ethyl, isopropyl or tert.-butyl radical or is the radical:

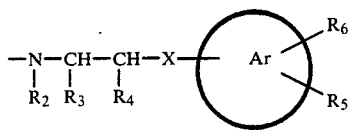

in which $R_2$ is a hydrogen atom, a lower alkyl radical or a benzyl, phenylethyl or phenylpropyl radical, $R_3$ is a hydrogen atom or a lower alkyl radical, $R_4$ is a hydrogen atom or a lower alky radical, X a valency bond, a —$CH_2$— group or an oxygen or sulphur atom, Ar is a phenyl, naphthyl, indanyl, tetrahydronaphthyl or pyridyl radical and $R_5$ and $R_6$, which can be the same or different, are hydrogen or halogen atoms, lower alkyl radicals, aminocarbonyl groups, hydroxyl groups, lower alkoxy radicals, benzyloxy radicals, lower alkylthio radicals, lower alkylsulphinyl radicals or lower alkylsulphonyl radicals or together represent a methylenedioxy radical.

The lower alkyl radicals $R_2$, $R_3$, $R_4$, $R_5$ and $R_6$ and the lower alkoxy, lower alkylthio, lower alkylsulphonyl or lower sulphonyl radicals $R_5$ and $R_6$ suitably have 1 to 6 preferably 1 to 4 carbon atoms.

Compounds with the above-mentioned substituents R are described in Federal Republic of Germany Patent Specification No. 22 40 599 and in European Patent Specification No. 4920.

According to the processes set out in these Patent Specifications, in all cases racemates of the described compounds are obtained. A separation of the racemate into the optically-active antipodes takes place according to per se known methods via a diastereomeric splitting with the use of known, optically-active acids or bases. This process is very laborious and, as a rule, does not give pure optically-active substances, contaminations due to the other antipodes being practically unavoidable.

Therefore, it is an object of the present invention to provide a synthesis route for the preparation of the antipodes in pure form.

Thus, according to the present invention, for the preparation of R-carbazole derivatives of general formula (I), an S-epoxide of the general formula:

in which $R_1$ is the residue of a substituted sulphonic acid derivative, is reacted with 4-hydroxycarbazole in the presence of an organic solvent in an alkaline medium and the R-4-(2,3-epoxypropoxy)-carbazole obtained is reacted with ammonia or a substituted amine of general formula RH, in which R has the same meaning as above, whereafter the compound obtained is, if desired, converted into a pharmacologically acceptable salt.

Substituted sulphonic acids in respect to $R_1$ are methanesulphonic acid, p-toluenesulphonic acid and benzenesulphonic acid.

The corresponding S-carbazole derivatives of general formula (I) are obtained in similar manner. For this purpose, R-(—)-epichlorhydrin is first reacted with 4-hydroxycarbazole in the presence of an organic solvent in an alkaline medium and the S-4-(2,3-epoxypropoxy)-carbazole obtained is reacted with ammonia or a substituted amine of the general formula RH, in which R has the same meaning as above, whereafter the compound obtained is, if desired, converted into a pharmacologically acceptable salt.

The preparation of the key compounds of general formula (II), preferably of the mesyl derivative, and of the R-(—)-epichlorhydrin are described in the literature (see Baldwin, J. org. Chem., 43, 4876/1978). According to this reference, D-mannitol is converted with acetone in the presence of zinc chloride into 1,2,5,6-di-O-isopropylidene-D-mannitol, splitting of which with sodium metaperiodate and subsequent immediate reduction of the intermediate aldehyde function formed gives S-(+)-isopropylidene-glycerol. Tosylation of this substance gives the R-3-tosyloxypropanediolacetonide which, without isolation, is immediately converted into R-(—)-3-tosyloxy-1,2-propanediol. From this, by reaction with sodium methylate, there is obtained R-glycidol which, because of the danger of racemisation, is immediately reacted with methanesulphonyl chloride to give S-(+)-3-mesyloxy-1,2-epoxypropane.

For the preparation of the R-(—)-epichlorhydrin, S-(+)-3-mesyloxy-1,2-epoxypropane is opened with hydrochloric acid to give R-1-chloro-2-hydroxy-3-mesyloxypropane which, without purification, is reacted in ethylene glycol with sodium methyleneglycolate to give R-(—)-epichlorhydrin.

The two mentioned key substances are each reacted with 4-hydroxycarbazole, with reversal of the configuration, to give the previously unknown R-(—)-4-(2,3-epoxypropoxy)-carbazole and S-(+)-4-(2,3-epoxypropoxy)-carbazole, which are also the subject of the present invention. The processes give both new antipodes with an optical purity of almost 100%.

The optically-active antipodes of 4-(2,3-epoxypropoxy)-carbazole are reacted, with maintenance of the configuration, with appropriate amines to give the optically-active compounds of general formula (I). For this purpose, as a rule, the carbazole derivative is heated under reflux for a comparatively long time with amine in an organic solvent, for example methanol, ethanol or isopropanol.

The optically-active carbazole derivatives of general formula (I) are new compounds. The pharmacological effectiveness of the particular antipodes is, in comparison with the racemate, greatly different. Whereas, for example, in the case of carvedilol, only S-(−)-(1-carbazole-4-yloxy)-3-[2-(2-methoxyphenoxy)]ethylaminopropan-2-ol (laevorotary isomer; Example 8) displays β-blocking properties, the vasodilatory action is present in both isomers of this compound (see the following experimental report). On the basis of this fact, the differing pharmacological properties are utilised in the development of pharmaceutical compositions.

By means of the freely selectable mixing ratios of the R and S-enantiomers, the particularly most favourable relationship of the two activity qualities can be objectively adjusted.

EXAMPLE

If, in the case of a racemate, the β-blockade, carried by the S-enantiomer, in comparison with the blood pressure lowering, carried by the R- and S-enantiomers, is too strong, then a more balanced activity relationship can be achieved by alteration of the proportion of the S-component.

Consequently, there can be used mixtures of R:S of from 1:99 to 99:1 except, in the meaning of the present invention, the ratio of 50:50 (racemate).

EXPERIMENTAL PROTOCOL

The β-blocking action was determined on awake rabbits on the basis of the inhibition of isoprenaline tachycardia (according to the method of Bartsch et al. (Experiments in animals on the pharmacological effects of metipranolol in comparison with propranolol and pindolol-Drug. Res., 27, (II), 12, 2319–2322/1977).

As a measure for the β-blocking activity strength, there was calculated the 50% inhibiting dosage.

VASODILATION (measured as direct blood pressure lowering after a single administration)

In awake, spontaneously hypertonic rats (SHR), catheters were implanted in the arteria femoralis and the vena jugularis. Via the veins, there were injected appropriate dosages of the enantiomers (R-carvedilol and S-carvedilol in dosages of 0.03; 0.1; 0.3; 1.0 and 3 mg/kg. i.v.) and the arterial blood pressure lowering was determined via the arterial pressure catheter (as an expression of the vasodilation). As a measure of the antihypertensive effect, there were calculated the dosages for lowering of the blood pressure by 30 mm.Hg.

RESULTS

The results of the investigations, not only with regard to the β-blockade but also to the blood pressure and blood vessel action, are summarised in the following Table:

TABLE

Action of R— and S—carvedilol on the heart (β-blockade) and blood vessels (blood pressure)

| purity % | β-blockade | | vasodilation | |
|---|---|---|---|---|
| | r | $ED_{50\%}$ (mcg/kg i.v.) | r | $ED_{-30mmHg}$ (mcg/kg i.v.) |
| R—carvedilol (>99.4%) | 0.96 | 3980 | 0.97 | 2960 |
| S—carvedilol (>99.4%) | 0.99 | 25 | 0.96 | 270 |
| relationship $\frac{R}{S}$ | — | 160 | — | 11 | carvedilol = (1-carbazol-4-yloxy)-3-[2-(2-methoxyphenoxy)]-ethylaminopropan-2-ol; racemate According to the above results, with correlation coefficients (r) of from 0.96 to 0.99, there is given a very good dosage action relationship. With regard to the β-blockade, between the two enantiomers there is such a great difference that practically only S-carvedilol can be regarded as being a β-blocker. Only at a 160 fold higher dosage is a β-blockade detectable for R-carvedilol, which is possibly to be attributable to traces of S-carvedilol.

With regard to the blood pressure lowering action, a comparatively small difference is ascertainable between S- and R-carvedilol. The difference factor is 11 and the absolutely necessary dosage in order to achieve a blood pressure lowering of 30 mm.Hg is, in the case of S-carvedilol with 270 mcg./kg. i.v., in comparison to the β-blockade, about 10 times higher.

A further particularity of the different pharmacological properties of the enantiomers of a compound of general formula (I) is that only the R-enantiomers display an outstanding antiglaucoma action and, therefore, can be used as optically pure substances for the treatment of glaucoma.

For the conversion of the compounds of general formula (I) into their pharmacologically acceptable salts, these are reacted, preferably in an organic solvent, with the equivalent amount of an inorganic or organic acid, for example hydrochloric acid, hydrobromic acid, phosphoric acid, sulphuric acid, acetic acid, citric acid, maleic acid or benzoic acid.

For the preparation of pharmaceutical compositions, the compounds of general formula (I) are mixed in known manner with appropriate pharmaceutical carrier materials, aroma, flavouring and colouring materials and formed, for example, into tablets or dragees or, with the addition of appropriate adjuvant materials, suspended or dissolved in water or an oil, for example olive oil.

For the treatment of glaucoma, compounds of general formula (I) or their pharmacologically acceptable salts are used in the form of eye drops. It is preferred to use salts with physiologically acceptable inorganic or organic acids, for example hydrochloric acid, hydrobromic acid, phosphoric acid, sulphuric acid, acetic acid, salicylic acid, citric acid, benzoic acid, naphthoic acid, o-acetoxybenzoic acid, adipic acid or maleic acid.

It is preferred to use isotonic solutions with a pH of about 7.0. As medium, it is preferred to use water which can contain conventional additives, such as preserving agents, solubilising agents or buffers. The preserving agent is preferably benzyl alcohol, benzalkonium chloride, phenol or chlorhexidine acetate. The solubilising agent is especially a polyethylene glycol, polyvinylpyrrolidone or glycerol. As buffers, it is preferable to use acetic acid/sodium acetate, citric acid/sodium citrate or sodium EDTA.

The compounds of general formula (I) according to the present invention and their salts can be administered enterally or parenterally in liquid or solid form. As injection medium, water is preferably used which contains the additives usual in the case of injection solutions, such as stabilising agents, solubilising agents or buffers. Such additives are, for example, tartrate and citrate buffers, ethanol, complex formers (such as ethylenediamine-tetraacetic acid and its non-toxic salts) and high molecular weight polymers (such as liquid polyethylene oxide) for viscosity regulation. Solid carrier materials are, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavouring and sweetening materials.

The following Examples are given for the purpose of illustrating the present invention:

EXAMPLE 1

S-(+)-3-Mesyloxy-1,2-epoxypropane 10.5 g. R-Glycidol are dissolved in a mixture of 23.3 ml. triethylamine and 210 ml. anhydrous toluene. To this is added dropwise at 0° to 5° C., with stirring, a solution of 11.5 ml. methanesulphonyl chloride in 50 ml. anhydrous toluene, whereafter the reaction mixture is left to stand overnight in a refrigerator. It is then filtered off with suction and the filtrate is evaporated in vacuo. The residue is dissolved in methylene chloride, the solution is washed with 1N hydrochloric acid, saturated aqueous sodium hydrogen carbonate solution and water, dried over anhydrous sodium sulphate and evaporated. The residue is distilled. Yield: 9 g. S-(+)-3-mesyloxy-1,2-epoxypropane; b.p.: 100° C./0.8 mm.Hg; $[\alpha]_D^{20}$: +24.2° (c=2.9; methanol).

The R-glycidol used is prepared as follows:

(a) 1,2,5,6-Di-O-isopropylidene-D-mannitol

To 2350 ml. acetone dried over neutral aluminium oxide are added 200 ml. molecular sieve 3 Å. 456 g. Zinc chloride are slowly introduced, while stirring, the solution thereby warming up slightly, whereafter the reaction mixture is left to stand overnight at ambient temperature. Subsequently, 285 g. D-(−)-mannitol are introduced, while stirring, and stirring is continued for 3 hours at ambient temperature, the mannitol thereby going into solution. The reaction mixture is filtered with suction, the filter residue is washed with a little dry acetone and the solution is immediately added, with stirring, to a mixture of 570 g. potassium carbonate, 600 ml. water and 1700 ml. diethyl ether. Precipitated zinc carbonate is filtered off and the filtrate is evaporated. The residue is taken up in methylene chloride and the water still present is separated off. Subsequently, the methylene chloride solution is dried over anhydrous sodium sulphate, treated with fuller's earth (floridin) and substantially evaporated. 3 Liters cyclohexane are then added thereto and left to crystallise. For further purification, the residue is again recrystallised from cyclohexane. Yield: 200 g. 1,2,5,6-di-O-isopropylidene-D-mannitol; m.p. 120°–121° C.

(b) S-(+)-Isopropylidene-glycerol

To a solution of 199 g. sodium metaperiodate in 1680 ml. water is added portionwise, with stirring and ice cooling, in the course of 45 minutes, 244 g. 1,2,5,6-di-O-isopropylidene-D-mannitol. After the addition is complete, stirring is continued for 15 minutes and then 5 liters ethanol are added thereto. The reaction mixture is filtered off with suction, the filter residue is then washed with ethanol and the filtrate is mixed, with slight cooling, in the course of 5 minutes, with 71 g. sodium borohydride.

After further stirring for 2 hours at ambient temperature, the pH value is adjusted with semiconcentrated acetic acid to 7.5. The mixture is left to stand for 15 minutes and then filtered off with suction. The filter residue is discarded and the filtrate is evaporated to such an extent that no more alcohol passes over. The remaining aqueous solution is extracted several times with methylene chloride. The combined methylene chloride phases are dried over anhydrous sodium sulphate and evaporated. The residue is distilled over a 40 cm. Vigreux column. Yield: 198.5 g. S-(+)-isopropylidene-glycerol; b.p. 45° C./0.7 mm.Hg; $[\alpha]_D^°$: +11.6° (c=10; methanol); $[\alpha]_D^{20}$: +15.1° (c=100).

(c) R-(−)-3-Tosyloxypropane-1,2-diol

To an ice-cold solution of 36 g. S-(+)-isopropylidene-glycerol in 150 ml. anhydrous pyridine is added portionwise, with stirring, 52 g. p-toluenesulphonyl chloride. After completion of the addition, the mixture is left to stand overnight in a refrigerator. The solution is then diluted with 150 ml. diethyl ether and washed with 1N hydrochloric acid until the aqueous phase has an acidic pH value, a total of about 600 ml. 1N hydrochloric acid being needed. Subsequently, the solution is washed twice with saturated aqueous sodium hydrogen carbonate solution, dried over anhydrous sodium sulphate, treated with floridin and evaporated. There are obtained 69.1 g. of an oily residue of R-3-tosyloxypropanediol acetonide which, without further purification, is further reacted. The acetonide is warmed to 80° C. in a mixture of 50 ml. acetone and 147 ml. 1N hydrochloric acid for 40 minutes, a clear solution being obtained. The solution is evaporated in vacuo and the residue is dissolved in methylene chloride. The methylene chloride solution is dried over anhydrous sodium sulphate and evaporated. The residue is recrystallised from diisopropyl ether. Yield: 45 g. R-(−)-3-tosyloxypropane-1,2-diol; m.p.: 62° C.; $[\alpha]_D^{20}$: −9.9° (c=7.9; methanol); $[\alpha]_D^{20}$: −6.8° (c=7.5; pyridine).

(d) R-Glycidol 45 g. R-(−)-3-Tosyloxypropane-1,2-diol are dissolved in a mixture of 40 ml. anhydrous methanol and 75 ml. anhydrous diethyl ether. To this is added dropwise, with stirring, at 0° to 5° C., within the course of 20 minutes, a solution of 4 g. sodium in 90 ml. methanol. The reaction mixture is further stirred for 2 hours and filtered off with suction. The filter residue is washed with diethyl ether and the filtrate is evaporated in vacuo at a bath temperature of 20° C. The residue is again taken up in diethyl ether and the solution treated with floridin, filtered off over Celite and evaporated. 10.5 g. R-glycidol are obtained as on oily residue. This is immediately further reacted in order to avoid a racemisation.

EXAMPLE 2

R-(−)-Epichlorhydrin

To 32.7 g. (+)-3-mesyloxy-1,2-epoxypropane are added dropwise, with good cooling, 130 ml. concentrated hydrochloric acid. After completion of the addition, stirring is continued for 30 minutes at ambient temperature and the solution is then evaporated at a bath temperature of 30° C. After removal of remaining amounts of water, the solution is evaporated several times after the addition of ethanol. The last residues of solvent are removed by application of a high vacuum. There are thus obtained 40.4 g. R-1-chloro-2-hydroxy-3-mesyloxypropane. This is dissolved in 105 ml. dry ethylene glycol. After the addition of a solution of 5.2 g. sodium in 130 ml. dry ethylene glycol, the mixture is further stirred for 15 minutes at ambient temperature. The resultant R-(−)-epichlorhydrin is immediately distilled from the reaction solution by the application of high vacuum (0.1–0.2 mm.Hg) at ambient temperature. For the condensation of the R-(−)-epichlorhydrin, the cooler is supplied with a cooling brine with a temperature of −40° to −50° C. The collecting flask is also cooled to this temperature. There are thus obtained 15.7 g. R-(−)-epichlorhydrin; yield: 78%; $[\alpha]_D^{20}$: −33.8° (c=1, methanol).

EXAMPLE 3

S-(+)-4-(2,3-Epoxypropoxy)-carbazole 27.5 g. 4-Hydroxycarbazole are dissolved in a mixture of 150 ml. 1N aqueous sodium hydroxide solution and 70 ml. dimethyl sulphoxide. To this is added at ambient temperature 13.9 g. R-(−)-epichlorhydrin, followed by stirring for 18 hours at ambient temperature. 280 ml. Water are then added thereto, followed by stirring for 15 minutes and filtering off with suction. The filter residue is washed with 0.1N aqueous sodium hydroxide solution and water and subsequently dissolved in methylene chloride. The methylene chloride solution is dried over anhydrous sodium sulphate, treated with active charcoal and floridin and evaporated. The residue is purified by recrystallising twice from ethyl acetate. Yield: 15.2 g. S-(+)-4-(2,3-epoxypropoxy)-carbazole; m.p.: 163°–164° C.; $[\alpha]_D^{20}$: +64.4° (c=1; pyridine).

From the mother liquors, there are isolated a further 6.7 g. of product; m.p.: 163°–164° C.; $[\alpha]_D^{20}$: +64.5° (c=1, pyridine).

EXAMPLE 4

R-(−)-4-(2,3-Epoxypropoxy)-carbazole 21.9 g. 4-Hydroxycarbazole are dissolved in a mixture of 120 ml. 1N aqueous sodium hydroxide solution and 40 ml. dimethyl sulphoxide. To this is added dropwise, at ambient temperature, a solution of 18.2 g. S-(+)-3-mesyloxy-1,2-epoxypropane in 20 ml. dimethyl sulphoxide. The mixture is stirred for 7 hours at ambient temperature, 225 ml. water are added thereto, further stirred for 15 minutes and filtered off with suction. The filter residue is washed with 0.1N aqueous sodium hydroxide solution and water and subsequently dissolved in methylene chloride. The methylene chloride phase is dried over anhydrous sodium sulphate, treated with active charcoal and floridin and evaporated. The residue is purified by recrystallising twice from ethyl acetate. Yield: 18.5 g. R-(−)-4-(2,3-epoxypropoxy)carbazole; m.p.: 162°–163° C.; $[\alpha]_D^{20}$: −63.4° (c=1; pyridine).

EXAMPLE 5

S-(−)-(1-Carbazol-4-yloxy)-3-isopropylaminopropan-2-ol hydroacetate 500 mg. S-(+)-4-(2,3-Epoxypropoxy)-carbazole are dissolved in 4 ml. methanol and, after the addition of 2.8 ml. isopropylamine, the solution is heated to 65° C. for 2 hours. It is then evaporated to dryness, taking care that no more isopropylamine is present. The residue is dissolved in 10 ml. hot ethyl acetate and the solution is mixed with 0.24 ml. glacial acetic acid. Upon cooling, S-(−)-carbazole hydroacetate crystallises out. The precipitate is filtered off, washed with ethyl acetate and dried. Yield: 410 mg.; m.p.: 158°–160° C.; $[\alpha]_D^{20}$: −20.1° (c=1; glacial acetic acid); optical purity according to gas chromatography findings: 99.5%.

EXAMPLE 6

R-(+)-(1-Carbazol-4-yloxy)-3-isopropylaminopropan-2-ol hydroacetate 18 g. R-(−)-4-(2,3-Epoxypropoxy)-carbazole are dissolved in 140 ml. methanol and, after the addition of 100 ml. isopropylamine, the solution is heated to 65° C. for 2 hours. The solution is then evaporated to dryness, further dried for 1 hour in high vacuum for the removal of residual isopropylamine and the residue is dissolved in 300 ml. hot ethyl acetate. The ethyl acetate solution is treated with floridin and, after suction filtration, mixed while still hot with 8.6 ml. glacial acetic acid. After cooling, the precipitated crystals are filtered off with suction. For further purification, the crystals are recrystallised from ethyl acetate, with the addition of a little methanol. Yield: 23 g. R-(+)-(1-carbazol-4-yloxy)-3-isopropylaminopropan-2-ol hydroacetate; m.p: 158°–160° C.; $[\alpha]_D^{20}$: +20.2° (c=1; glacial acetic acid); optical purity: 98.6%; chemical purity: 99.97%.

EXAMPLE 7

R-(+)-(1-Carbazol-4-yloxy)-3-[2-(2-methoxyphenoxy)-]ethylaminopropan-2-ol 5 g. R-(−)-4-(2,3-Epoxypropoxy)-carbazole are, together with 6.9 g. o-methoxyphenoxyethylamine, heated under reflux in 35 ml. isopropanol for 2 hours. The solvent is evaporated off and the residue is stirred for 2 hours with a mixture of 115 ml. toluene, 35 ml. cyclohexane and 40 ml. ethyl acetate. The reaction mixture is filtered off with suction and the residue is recrystallised from 150 ml. ethyl acetate. Yield: 3.7 g. R-(+)-(1-carbazol-4-yloxy)-3-[2-(2-methoxyphenoxy)]-ethylaminopropan-2-ol; m.p.: 121°–123° C.; $[\alpha]_D^{20}$: +18.4° (c=1; glacial acetic acid).

EXAMPLE 8

S-(−)-(1-Carbazol-4-yloxy)-3-[2-(2-methoxyphenoxy)-]ethylaminopropan-2-ol 10 g. S-(+)-4-(2,3-Epoxypropoxy)-carbazole are, together with 13.97 g. o-methoxyphenoxyethylamine, heated under reflux in 70 ml. isopropanol for 2 hours. The solvent is evaporated off and the residue is stirred for 2 hours with a mixture of 115 ml. toluene, 35 ml. cyclohexane and 40 ml. ethyl acetate. After filtering off with suction, the residue is recrystallised from 150 ml. ethyl acetate. Yield: 7.2 g. S-(−)-(1-carbazol-4-yloxy)-

3-[2-(2-methoxyphenoxy)]-ethylaminopropan-2-ol; m.p. 121°–123° C.; $[\alpha]_D^{20}$: $-18.4°$ (c=1; glacial acetic acid).

It will be understood that the specification and examples are illustrative but not limitative of the present invention and that other embodiments within the spirit and scope of the invention will suggest themselves to those skilled in the art.

What is claimed is:

1. A process for the preparation of an R-carbazole derivative of the formula:

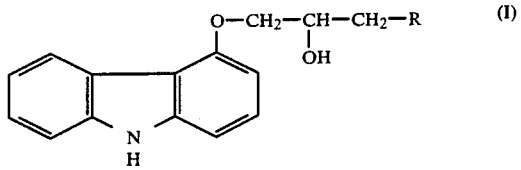

or its pharmacologically acceptable salts wherein
R is an amino group, an amino group substituted by a lower alkyl radical, or the radical:

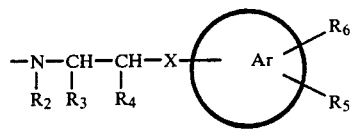

in which $R_2$ is a hydrogen atom, lower alkyl, benzyl, phenylethyl or phenylpropyl; $R_3$ is a hydrogen atom or lower alkyl; $R_4$ is a hydrogen atom or lower alkyl; X is a valency bond, a —$CH_2$— group, or an oxygen or sulphur atom; Ar is a phenyl, naphthyl, indanyl, tetrahydronaphthyl or pyridyl; and $R_5$ and $R_6$, which can be the same or different, are hydrogen or halogen atoms, lower alkyl, aminocarbonyl, hydroxyl, lower alkoxy, benzyloxy, lower alkylthio, lower alkylsulphinyl or lower alkylsulphonyl or together represent methylenedioxy;
comprising the steps of reacting an S-epoxide derivative of the formula:

in which $R_1$ is the residue of a substituted sulphonic acid derivative selected from the group consisting of methanesulphonic acid, p-toluenesulphonic acid and benzenesulphonic acid, with 4-hydroxycarbazole in the presence of an organic solvent selected from the group consisting of dimethylsulfoxide, dimethyl formamide and dioxane in an alkaline medium; and reacting the R-4-(2,3-epoxypropoxy)-carbazole obtained, with ammonia or a substituted amine of the formula RH, in which R has the same meaning as above;

thereafter recovering the R-carbazole derivative or converting the carbazole derivative into a pharmacologically acceptable salt and recovering said salt.

2. Process according to claim 1, wherein R is an isopropylamine, tert.-butylamine or o-methoxyphenoxy-ethylamine radical and $R_1$ is a mesyl radical.

* * * * *